United States Patent [19]

Holinej

[11] Patent Number: 4,970,078

[45] Date of Patent: Nov. 13, 1990

[54] CROSSLINKED CARBOXYMETHYGUAR TABLET DISINTEGRANT

[75] Inventor: Jurij Holinej, Newark, Del.

[73] Assignee: Aqualon Company, Wilmington, Del.

[21] Appl. No.: 356,852

[22] Filed: May 25, 1989

[51] Int. Cl.$^5$ ................................................ A61K 9/20
[52] U.S. Cl. .................................. 424/465; 424/469; 424/414
[58] Field of Search .............................. 424/465, 469

[56] References Cited

U.S. PATENT DOCUMENTS

| | | | |
|---|---|---|---|
| 4,109,018 | 8/1978 | Thompson | 426/19 |
| 4,209,513 | 6/1980 | Torode et al. | 514/158 |
| 4,349,531 | 9/1982 | Mlodozeniec | 424/443 |

FOREIGN PATENT DOCUMENTS 0281360  1/1988  European Pat. Off. ................ 37/14

OTHER PUBLICATIONS

"Carboxymethylated Galactomannan Products as Pharmaceutical Adjuvants. 2. Microscopic Studies and Water-Absorption Properties".

Primary Examiner—Merrell C. Cashion, Jr.
Assistant Examiner—Leon R. Horne
Attorney, Agent, or Firm—James K. Luchs

[57] ABSTRACT

Tablets containing 1–2% by weight carboxymethylguar as a disintegrant are equivalent to tablets containing sodium carboxymethylcellulose in medicant release. These tablets can be made at a lower cost while still meeting Pharmacopeia standards.

2 Claims, No Drawings

CROSSLINKED CARBOXYMETHYGUAR TABLET DISINTEGRANT

FIELD OF THE INVENTION

The invention relates to pharmaceutical tablets which disintegrate in water to release medication. In particular, the invention relates to crosslinked carboxymethyl guar as a tablet ingredient to achieve disintegration of a tablet.

BACKGROUND OF THE INVENTION:

Guar is a leguminous plant from which a guar gum is extracted. Chemically, guar gum is a galactomannan which is a polysaccharide polymer with a galactose on every other unit of a mannose repeating backbone. Purified and chemically modified guars have gained utility as thickening agents and food additives.

E. Nuernberg et al., "Carboxymethylated Galactomannan Products as Pharmaceutical Adjuvants", Acta Pharmaceutica Technologia, 30(1), pp. 50–55, 1984, discloses that carboxymethylated guar absorbs more water than natural guar when the two materials are held at the same relative humidity. U.S. Pat. No. 4,109,018 discloses that guar gum can be used to produce a low calorie diet bread. European patent application EPO 0 281 360 discloses hydrophobically modified non-ionic polygalactomannan ethers which are useful as thickening agents for aqueous systems.

It is known in the art to use an acid crosslinked carboxymethylcellulose identified as croscarmellose sodium, type A, NF or crosslinked polyvinyl pyrrolidone or sodium starch glyconate in the manufacture of disintegrating tablets. Yet in spite of an ongoing need for an alternative to the predominate use of crosslinked carboxymethylcellulose for this application, There was no suggestion in the art that a new and cost effective substance could be substituted for the long established crosslinked carboxymethylcellulose.

SUMMARY OF THE INVENTION

It is an object of the invention to use crosslinked carboxymethylpolygalactomannan in tablets which disintegrate in water to release medication.

A preferred tablet ingredient is carboxymethylguar with a degree of substitution between 0.17 and 0.21 which is crosslinked with concentrated HC1.

A preferred tablet formulation comprises:

| | |
|---|---|
| Crosslinked carboxymethylguar | 2 to 10 mg |
| Magnesium stearate, NF | 1 to 5 mg |
| Fast Flo TM Lactose, NF | 100 to 140 mg |
| Dicalcium phosphate dihydrate, NF | 100 to 140 mg |
| Medicant, USP | 30 to 80 mg |

Tablets containing crosslinked carboxymethylguar are lower in cost than tablets containing crosslinked carboxymethylcellulose.

DETAILED DESCRIPTION OF THE INVENTION

The United States Pharmacopeia, Official from Jan. 1985, details allowable dissolution rates for tablets and test apparatus and procedures. Thus, a tablet which did not meet these standards would not be acceptable.

It has been discovered that crosslinked carboxymethylguar is a new material for tablet formulation which can give equivalent performance to crosslinked carboxymethylcellulose in tablets meeting the Pharmacopeia standards. This was indeed a surprising result in view of a complete absence of knowledge by persons skilled in the art that it would be possible to use a lower cost material.

The use of crosslinked carboxymethylcellulose in tablet manufacture is known from published literature such as Wan and Prasad, *Effect of Microcrystalline Cellulose and Crosslinked Sodium Carboxymethylcellulose on the Properties of Tablets with Methylcellulose as a Binder*, International Journal of Pharmaceutics, 41, (1988) 159–167.

A formula for a disintegrating tablet comprising crosslinked carboxymethylcellulose published in FMC Corporation Bulletin SD-1 contains the following:

| | |
|---|---|
| Croscarmellose sodium, type A, NF | 6 mg |
| Magnesium stearte, NF | 3 mg |
| Fast Flo TM Lactose, NF | 123 mg |
| Dicalcium phosphate, NF | 123 mg |
| Hydrochlorothiazide, USP | 45 mg |

According to the practice of the present invention, a crosslinked polygalactomannan can be substituted for croscarmellose sodium in this 6 mg formulation as well as a 9 mg or 30 mg formulation.

A crosslinked polygalactomannan suitable for the practice of the invention can be produced by reacting a guar gum with monochloracetic acid under caustic conditions. After reaction the polygalactomannan is crosslinked with hydrochloric acid.

In a grade suitable for pharmaceutical use a crosslinked carboxymethylguar with a degree of substitution of about 0.10 to 0.20 is an off-white powder, 90% of which is capable of passing through a 140 mesh sieve. Typical viscosities for a 1% solution of crosslinked carboxymethylguar at 25° C. range from 500 to 900 cps.

The present invention has industrial applicability in the pharmaceutical field for the production of tablets which disintegrate in water or an acid medium such as in the stomach or a mild alkaline medium such as the intestine.

The following examples illustrate the practice of the invention without limitation to any particular medication or dosage form. Test procedures used in these examples are derived from The United States Pharmacopeia USP XXI which is incorporated by reference.

EXAMPLE 1

Supercol ™ guar gum available from Aqualon, Wilmington, DE, was reacted with monochloracetic acid under caustic conditions to provide a degree of substitution of 0.17 to 0.21. A carboxymethylguar was recovered, washed and dried to produce a white powder.

Crosslinking of the CM-guar was done by reacting concentrated HC1 (36.5%) with CM-guar in an aqueous acetone diluent. The material was filtered, washed and dried at 75° C. under vacuum for four hours. The ratio of HC1, the crosslinking agent, to CM-guar was 1:19.3.

Control and experimental tablets were prepared in which hydrochlorothiazide (HCTZ) was chosen as a model drug because it is relatively water-insoluble and has poor dissolution.

| Ingredient | Control | Invention | Prior Art |
|---|---|---|---|
| Hydrochlorothiazide, USP | 50.0 | 50.0 | 50.0 |

-continued

| Ingredient | Control | Invention | Prior Art |
|---|---|---|---|
| Dicalcium phosphate, dihydrate, NF | 123.5 | 120.5 | 120.5 |
| Fast Flo ™ Lactose, NF | 123.5 | 120.5 | 120.5 |
| Croscarmellose sodiu, Type A, NF | — | — | 6.0 |
| Crosslinked carboxymethylguar | — | 6.0 | — |
| Magnesium stearate, NF | 3.0 | 3.0 | 3.0 |
| Total Tablet Weight mg. | 300.0 | 300.0 | 300.0 |

To prepare the tablets, all ingredients except magnesium stearate were passed through a 20 mesh screen and then blended for 5 minutes in a V-blender. The magnesium stearate was passed through a 20 mesh screen and then blended with the other ingredients for 2 minutes. The powder blend was compressed into tablets of 6 and 12 Kp hardness using 5/16 inch standard concave tooling.

Disintegration and dissolution tests were performed in both distilled water and 0.1 N HC1. USP Apparatus I was used for the dissolution test run for 75 minutes. The initial speed was 100 rpm but the speed was increased to 150 rpm during the last 15 minutes. An automated sampler was used to take samples at 5, 10, 20, 30, 45, 60, and 75 minutes. The samples were analyzed by UV spectrophotometry. Table 1 contains comparative results.

TABLE 1

| Disintegrant | kp | Dissolution Times in Minutes 85%* | |
|---|---|---|---|
| | | Water | 0.1 N HCl |
| None | 6 | 505 | 122 |
| None | 12 | 554 | 168 |
| Prior Art | 6 | 23 | 10 |
| Prior Art | 12 | 32 | 15 |
| Invention | 6 | 30 | 10 |
| Invention | 12 | 28 | 15 |

*Note: USP requirement for HCTZ is 60% in 30 minutes

As shown in Table 1, crosslinked carboxymethylguar used in the same manner as the prior art disintegrant, crosslinked carboxymethylcellulose, gives comparable results. While the control tablet took over five minutes to disintegrate, both the prior art and invention tablets with a 6 kp hardness effectively disintegrated in one minute. While the 12 kp tablet of the invention was observed to be slower in disintegrating than the 12 kp prior art tablet, Table 1 clearly shows that the medicinal release was equivalent. Because guar is a lower cost component than croscarmellose sodium and the other tablet components are the same, it was possible to produce a lower cost tablet.

EXAMPLE 2

Tablets were prepared as in Example 1 except that both 1% and 2% by weight disintegrant was used in the formulation. Dissolution and disintegration tests were run on tablet samples as in Example 1. Using the automated sample data it was possible to prepare plots of dissolution versus time.

A review of plots of the data confirmed the results of Example 1. In many cases the 6 kp tablets of both the invention and prior art gave identical results.

In proper perspective, all the data obtained has shown that the tablets prepared according to the invention pass the 30 minute dissolution in 0.1 N HCl standard of the Pharmacopeia for hydrochlorothiazide tablets.

What is claimed is:

1. A pharmacentical tablet comprising hydrochlorothiazide and crosslinked carboxymethyl guar, said guar being crosslinked with HCl, said guar comprising 1 to 2% by weight of the table and said guar having a degree of substitution between 0.17 and 0.21.

2. A table formulation comprising:

| HCl crosslinked carboxymethyl guar | 2-10 mg. |
|---|---|
| Magnesium stearate, NP | 1-5 mg. |
| Lactose, NF | 100-140 mg. |
| Dicalcium phosphate dihydrate, NF | 100-140 mg. |
| Hydrochlorothiazide, USP | 30-80 mg. |

* * * * *

UNITED STATES PATENT AND TRADEMARK OFFICE
CERTIFICATE OF CORRECTION

PATENT NO. : 4,970,078

DATED : Nov. 13, 1990

INVENTOR(S) : Juriji Holinej

It is certified that error appears in the above-identified patent and that said Letters Patent is hereby corrected as shown below:

ON THE TITLE PAGE:

(54) In the Title

"CARBOXYMETHYGUAR" should read -- CARBOXYMETHYLGUAR --

Column 1, Line 1, title

"CARBOXYMETHYGUAR" should read -- CARBOXYMETHYLGUAR --

Column 1, Line 36

"There" should read -- there --

Column 2, Line 18

"stearte" should read -- stearate --

Column 3, Line 6

"sodiu," should read -- sodium --

Column 4, Line 28 (Claim 1)

"pharmacentical" should read -- pharmaceutical --

UNITED STATES PATENT AND TRADEMARK OFFICE
CERTIFICATE OF CORRECTION

PATENT NO. : 4,970,078

DATED : Nov. 13, 1990

INVENTOR(S) : Juriji Holinej

It is certified that error appears in the above-identified patent and that said Letters Patent is hereby corrected as shown below:

Column 4, Line 32 (Claim 1)

"table" should read -- tablet --

Column 4, Line 34 (Claim 2)

"table" should read -- tablet --

Signed and Sealed this

Eleventh Day of June, 1991

Attest:

*Attesting Officer*

HARRY F. MANBECK, JR.

*Commissioner of Patents and Trademarks*